(12) United States Patent
Miwa

(10) Patent No.: US 11,197,649 B2
(45) Date of Patent: Dec. 14, 2021

(54) MOBILE RADIATION IMAGING APPARATUS

(71) Applicant: Shimadzu Corporation, Kyoto (JP)

(72) Inventor: Takatoshi Miwa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/959,951

(22) PCT Filed: Nov. 2, 2018

(86) PCT No.: PCT/JP2018/040823
§ 371 (c)(1),
(2) Date: Jul. 2, 2020

(87) PCT Pub. No.: WO2019/181055
PCT Pub. Date: Sep. 26, 2019

(65) Prior Publication Data
US 2021/0186441 A1     Jun. 24, 2021

(30) Foreign Application Priority Data
Mar. 23, 2018  (JP) .............................. JP2018-055460

(51) Int. Cl.
*A61B 6/00*     (2006.01)
*A61B 6/10*     (2006.01)

(52) U.S. Cl.
CPC ............ *A61B 6/4405* (2013.01); *A61B 6/105* (2013.01)

(58) Field of Classification Search
CPC .............................. A61B 6/105; A61B 6/4405
See application file for complete search history.

(56) References Cited

U.S. PATENT DOCUMENTS

2011/0096910 A1* 4/2011 Yao ........................ A61B 6/105
378/197

FOREIGN PATENT DOCUMENTS

JP    2008-173256 A    7/2008
JP    2011-212497 A    10/2011

OTHER PUBLICATIONS

Written Opinion for PCT application PCT/JP2018/040823 dated Jan. 15, 2019, submitted with a machine translation.

* cited by examiner

*Primary Examiner* — Dani Fox
(74) *Attorney, Agent, or Firm* — Muir Patent Law, PLLC

(57) ABSTRACT

A travel handle (20) is provided with a pair of support plates (22) and a gripping bar (21) extended between the support plates (22). The pair of support plates (22) has a groove-like shape and is engaged with a slider (25) provided to a main body so that the support plates are reciprocally guided in a longitudinal direction inclined relative to the horizontal direction, and the reciprocal motion ends of the support plate in the reciprocating direction are regulated. The slider (25) is provided with a braking roller in contact with a groove portion side surface of the support plate (22) of the travel handle (20) and a braking control mechanism (26) for performing control such that the braking force by the travel handle (20) against the upward/downward movement of the travel handle (20) in the inclined direction is increased when the travel handle (20) is moved downward and decreased when the travel handle (20) is moved upward.

3 Claims, 5 Drawing Sheets

MOBILE RADIATION IMAGING APPARATUS

TECHNICAL FIELD

The present invention relates to a mobile radiation imaging apparatus.

BACKGROUND OF THE INVENTION

A mobile X-ray imaging apparatus, which is one type of such a mobile radiation imaging apparatus, is also called an X-ray imaging apparatus for rounds, and performs X-ray imaging by traveling between hospital rooms. The mobile X-ray imaging apparatus is provided with the main body having a front wheel and a rear wheel, a support provided to a main body in an upright posture, an ascendable/descendable member configured to move upward and downward along the support in a state in which an X-ray irradiation unit composed of an X-ray tube and a collimator are supported, an X-ray detector configured to detect X-rays emitted from the X-ray irradiation unit and passed through a subject, and a battery mounted on the main body.

When moving such a mobile X-ray imaging apparatus, an operator grasps a travel handle attached to the main body and moves the apparatus in any orientation. At this time, the travel handle of the mobile X-ray imaging apparatus is fixed at a position suitable for an operator of an average body size. For this reason, for an operator with a relatively high height, the moving operation needs to be performed in a posture in which the position of the travel handle is low and the back of the user is bent. For an operator with a relatively low height, the position of the travel handle is high and therefore it is difficult to perform the traveling operation.

For this reason, there has also been proposed an X-ray imaging apparatus for rounds in which the travel handle is configured to be movable along rails so that the travel handle can be fixed at a height position suitable for the traveling operation in accordance with the height of an operator (see Patent Document 1 and Patent Document 2).

PRIOR ART DOCUMENT

Patent Document

Patent Document 1: Japanese Unexamined Patent Application Publication No. 2008-173256
Patent Document 2: Japanese Unexamined Patent Application Publication No. 2011-212497

SUMMARY OF THE INVENTION

Problems to be Solved by the Invention

In cases where a configuration is adopted in which the height position of the travel handle can be changed by moving the travel handle upward and downward as described above, for example, it can be configured such that the travel handle is provided to rails so as to be movable along sliders provided to a main body. At this time, since the travel handle has, for example, a weight of about 3 Kg, it is preferable to configure such that when moving the travel handle downward, the weight of the travel handle is held, so that the travel handle can be gradually moved downward, and when moving the travel handle upward, no load other than the weight of the travel handle is generated.

The present invention has been made to solve the above-described problems, and it is an object of the present invention to provide a mobile radiation imaging apparatus capable of moving a travel handle having a predetermined weight upward and downward with an appropriate force.

Means for Solving the Problem

According to the invention as recited in claim 1, a mobile radiation imaging apparatus is provided with a main body having wheels, a support provided to the main body in an upright posture, a radiation irradiation unit supported by the support, and a travel handle used when the main body is traveled. The mobile radiation imaging apparatus includes: a guide member provided to the main body to support the travel handle in an ascendable and descendable manner; a braking roller provided to the main body in such a manner as to be in contact with the travel handle; and a braking control mechanism configured to perform control such that braking force by the braking roller against an upward/downward movement of the travel handle is increased when the travel handle is moved downward and decreased when the travel handle is moved upward.

According to the invention as recited in claim 2, in the mobile radiation imaging apparatus as recited in claim 1, the braking roller has an outer peripheral region formed of an elastic member in contact with the travel handle, and the braking control mechanism includes: a load mechanism configured to apply a load to rotation of the braking roller; and a swing support mechanism configured to support the braking roller in such a manner as to be swingable about a center of swing positioned lower than a contact region between the braking roller and the travel handle.

According to the invention as recited in claim 3, in the mobile radiation imaging apparatus as recited in claim 2, the swing support mechanism is provided to the main body in such a manner as to be rotatable about a center of rotation positioned lower than the contact region between the braking roller and the travel handle and is composed of an eccentric member having a shaft rotatably supporting the braking roller at a position eccentric from the center of rotation, and the load mechanism is composed of a clamping member configured to clamp the braking roller between the clamping member and the eccentric member with a braking force.

Effects of the Invention

According to the invention as recited in claim 1, the braking force against the upward/downward movement of the travel handle by the braking roller is controlled so that the braking force is increased when the travel handle is moved downward and decreased when the travel handle is moved upward. Therefore, it becomes possible to move the travel handle downward gradually, or to move the travel handle upward with a small load, which in turn can move the travel handle having a predetermined weight upward and downward by an appropriate force.

According to the present inventions as recited in claim 2, when moving the travel handle downward, the elastic region of the braking roller in contact with the travel handle is deformed to generate a frictional force at the time of rotation of the braking roller and a load is applied to the rotation by the load mechanism, so that a predetermined braking force is generated. When moving the travel handle upward, the braking roller is swung and its frictional force is reduced to eliminate the braking force. Therefore, the travel handle having a predetermined weight can be moved upward and downward by an appropriate force.

According to the invention as recited in claim 3, the swinging of the braking roller and the load to the braking roller can be realized in a small space by the eccentric member.

EMBODIMENTS FOR CARRYING OUT THE INVENTION

Figure 1:
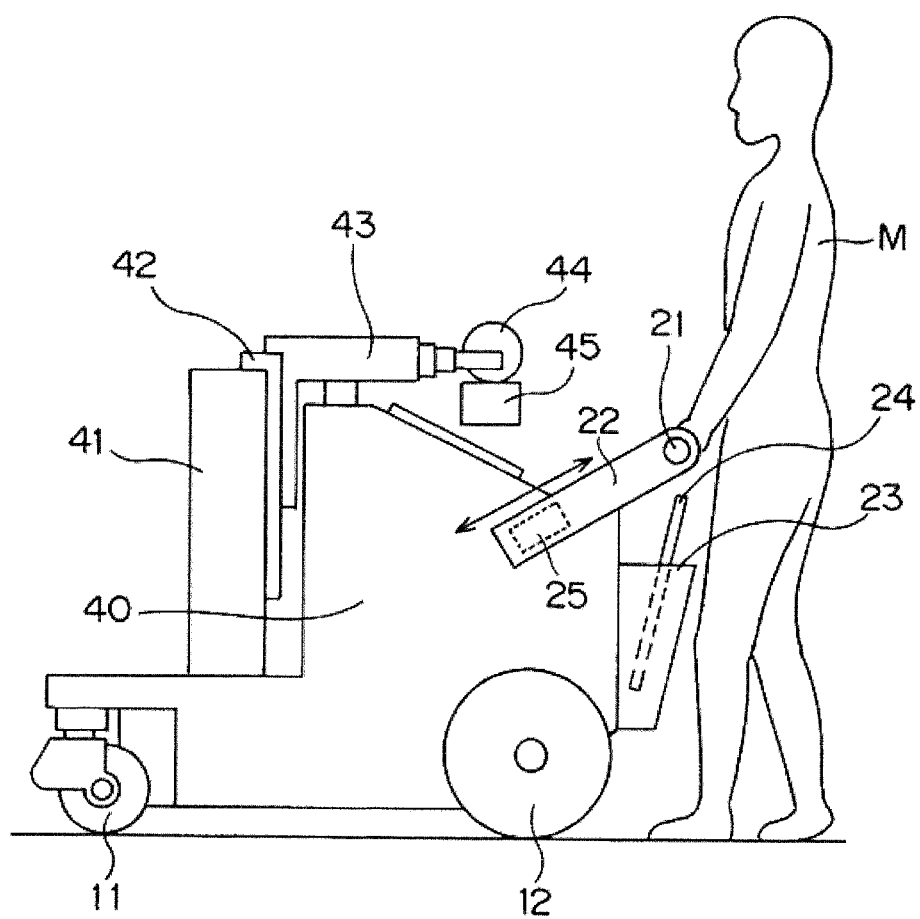
FIG. 1 is a side schematic view of a mobile X-ray imaging apparatus according to the present invention.

Hereinafter, embodiments of the present invention will be described with reference to the attached drawings. FIG. 1 is a schematic side view of a mobile X-ray imaging apparatus as a mobile radiation imaging apparatus according to an embodiment of the present invention disclosure.

This mobile X-ray imaging apparatus is also referred to as an X-ray imaging apparatus for rounds, and performs X-ray imaging by sequentially traveling between hospital rooms by the operation of an operator M. A pair of right and left front wheels 11 as wheels for changing the traveling direction is arranged on the front side of the main body 40 of this mobile X-ray imaging apparatus in the traveling direction. A pair of right and left rear wheels 12 as driving wheels is arranged on the rear side of the main body 40 of the mobile X-ray imaging apparatus.

On the front side of the main body 40 in the traveling direction, the support 41 is provided in an upright posture. Provided to this support 41 are a first ascendable/descendable member 42 and the second ascendable/descendable member 43 in an ascendable/descendable manner. The second ascendable/descendable member 43 has a substantially L-shaped shape in a side view, and is provided at a distal end portion thereof with an X-ray irradiation unit composed of an X-ray tube 44 and a collimator 45. The X-ray tube 44 and the collimator 45 is moved upward and downward in accordance with the upward/downward movement of the first ascendable/descendable member 42 and the second ascendable/descendable member 43. Further, the support 41 is supported rotatably about a vertical axis, and the X-ray tube 44 and the collimator 45 are rotated together with the second ascendable/descendable member 43 in accordance with the rotation of the support 41.

The main body 40 is provided with a travel handle 20 equipped with a gripping bar 21 and support plates 22 for operating the traveling direction of the main body 40 (see FIG. 2), and a storage unit 23 for accommodating an X-ray detector 24, such as, e.g., a flat panel detector for detecting X-rays irradiated from the X-ray tube 44 and passed through a subject. The support plates 22 of the travel handle 20 are reciprocally movable along a slider 25 provided to the main body 40.

Figure 2:
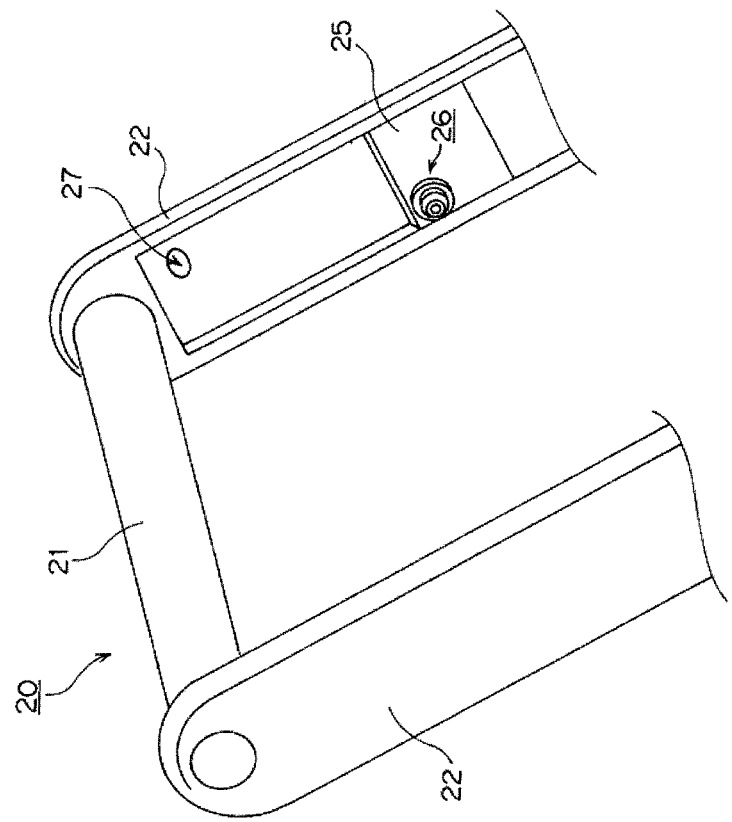
FIG. 2 is a perspective view of a travel handle 20 according to a first embodiment of the present invention.
Figure 3:
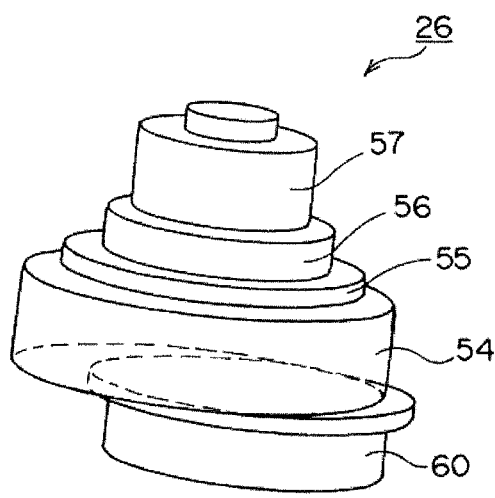
FIG. 3 is a perspective view of a braking control mechanism 26 according to the present invention.
Figure 4:
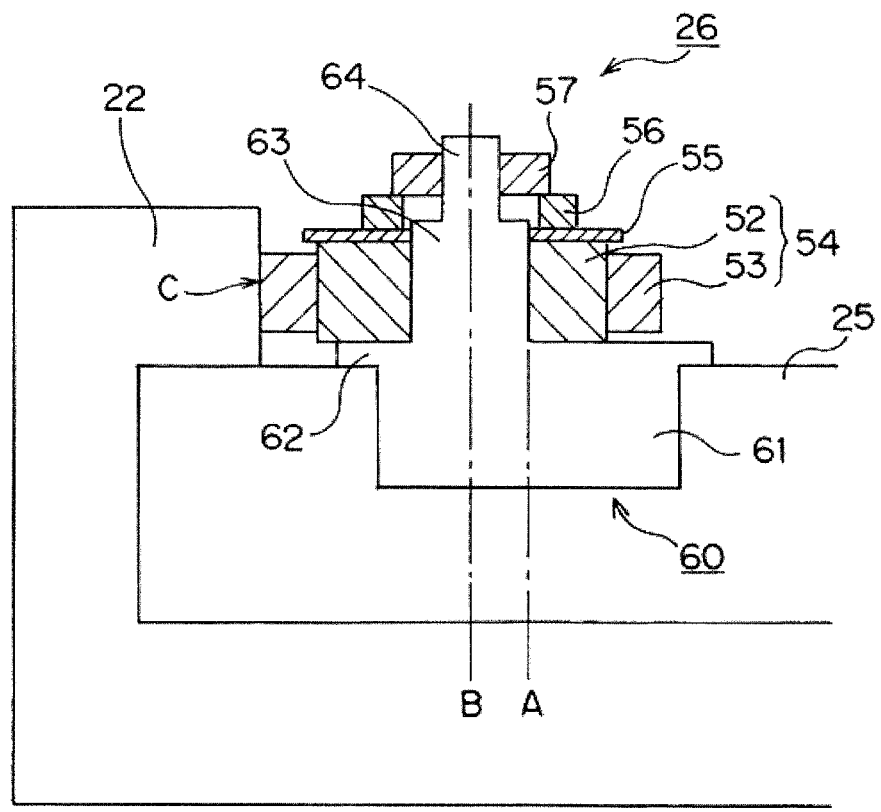
FIG. 4 is a cross-sectional view of a braking control mechanism 26 according to the present invention.
Figure 5:
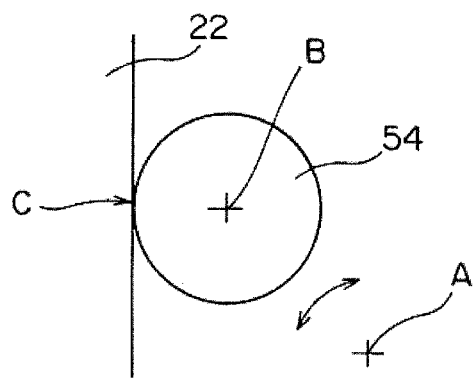
FIG. 5 is a diagram for explaining a contact region C between a braking roller 54 and the groove portion side surface of a support plate 22 of a travel handle 20 and an arrangement relationship between the center of swing A and the center of rotation B of a braking roller 54.

FIG. 2 is a perspective view of the travel handle 20 according to a first embodiment of the present invention. FIG. 3 is a perspective view of a braking control mechanism 26 according to the present invention. FIG. 4 is a cross-sectional view of the braking control mechanism 26 according to the present invention. FIG. 5 is a diagram for explaining a contact region C between a braking roller 54 and the groove portion side surface of the support plate 22 of the travel handle 20 and an arrangement relationship between the center of swing A and the center of rotation B of the braking roller 54.

This travel handle 20 is provided with a pair of support plates 22 and a gripping bar 21 connecting the support plates 22. The pair of support plates 22 each have a groove-like shape, and is engaged with a slider 25 provided to the main body 40 to be guided in a reciprocally movable manner in a longitudinal direction inclined with respect to the horizontal direction (the direction indicated by an arrow in FIG. 1), and is regulated in the reciprocating motion at the respective ends in the reciprocating direction. The slider 25 is provided with a braking roller 54 in contact with the groove portion side surface of the support plate 22 of the travel handle 20 and a braking control mechanism 26 for performing control so that the braking force against the upward/downward movement of the travel handle 20 in the inclined direction by the braking roller 54 is increased when the travel handle 20 is moved downward and decreased when the travel handle 20 is moved upward.

The braking control mechanism 26 is provided with a load mechanism for applying a load to the rotation of the braking roller 54 and a swing support mechanism for pivotally supporting the braking roller 54 about a center of swing A (see FIG. 5) positioned lower than the contact region C between the braking roller 54 and the groove portion side surface of the support plate 22 of the travel handle 20.

The swing support mechanism is provided with an eccentric member 60. The eccentric member 60 is provided to the main body 40 in such a manner so as to be rotatable about the center of rotation (i.e., the center of swing) A positioned lower than the contact region C between the braking roller 54 and the groove portion side surface of the support plate 22 of the travel handle 20. The eccentric member 60 is provided with a shaft 63 rotatably supporting the braking roller 54 at a position B eccentric from the center of rotation A. Further, the load mechanism is provided with a clamp member for clamping the braking roller 4 between the claim member and the flange portion 62 of the eccentric member 60.

That is, as shown in FIG. 4, the eccentric member 60 is provided rotatably about the center of rotation (the center of swing of the braking roller 54) with respect to the slider 25. This eccentric member 60 is composed of a rotation shaft portion 61, a flange portion 62, a shaft 63, and a threaded portion 64 in the order from the slider 25 side. The axis B of the shaft 63 is arranged at a position eccentric from the axis A of the rotation shaft portion 61. The braking roller 54 composed of a metallic inner peripheral region 52 and an outer peripheral region 53 made of an elastic member such as rubbers is arranged in such a manner as to be rotatable around the shaft 63.

A washer 55 and a disc spring 56 are arranged at the upper portion of the braking roller 54, and a screw 57 screwed to the threaded portion 64 of the eccentric member 60 is arranged at the top of the disc spring 56. By the action of the screw 57 and the disc spring 56, the braking roller 54 is clamped between the washer 55 and the flange portion 62 of the eccentric member 60 with a predetermined braking force. The screw 57, the disc spring 56, and the washer 55 constitute a clamping member for holding the braking roller 54 between the clamping member and the eccentric member 60 with a predetermined braking force.

As shown in FIG. 2, a plurality of holes 27 is formed on the support plate 22 of the travel handle 20 at constant pitches. Note that in FIG. 2, one of a plurality of holes 27 is illustrated. On the other hand, the slider 25 is provided with a pin (not shown) movable between the state of being engaged with the hole 27 and the state of being released from the hole 27. The action of the pin and the hole 27 enables to fix the ascendable/descendable travel handle 20 at a plurality of positions.

Next, an ascending/descending movement for causing the travel handle 20 to move the travel handle 20 having the above-described configuration obliquely downward or obliquely upward will be described.

When moving the travel handle 20 downward, an operator M attempts to move the gripping bar 21 of the travel handle 20 obliquely downward. With this, by the frictional force between the outer peripheral region 53 formed of an elastic member in the braking roller 54 and the groove portion side surface of the support plate 22 in the travel handle 20, the eccentric member 60 swings towards the direction to press the braking roller 54 against the groove portion side surface of the support plate 22 in the travel handle 20. With this, the braking roller 54 in which the outer peripheral region 53 is composed of an elastic member is deformed, so that the frictional force of the support plate 22 against the groove portion side surface of the travel handle 20 is increased, so that the weight of the travel handle 20 is held. When an operator M moves the gripping bar 21 of the travel handle 20 obliquely downward, the braking roller 54 rotates in a state in which the braking roller 54 is in contact with the groove portion side surface of the support plate 22 of the travel handle 20. At this time, the braking roller 54 rotates against the braking force acting by the screw 57, the disc spring 56, and the washer 55, so that the travel handle 20 is moved obliquely downward.

On the other hand, when moving the travel handle 20 upward, an operator M moves the gripping bar 21 of the travel handle 20 obliquely upward. With this, the eccentric member 60 swings in a direction to separate the braking roller 54 from the groove portion side surface of the support plate 22 of the travel handle 20. As a result, it becomes a state in which the braking roller 54 and the groove portion side surface of the support plate 22 of the travel handle 20 are only in contact with each other and almost no frictional force acts therebetween. Then, when an operator M is pulled the travel handle 20 obliquely upward, the travel handle 20 is moved obliquely upward against its own weight.

As described above, in the travel handle 20 according to the present invention, at the time of moving the travel handle 20 downward, by the action of the swing support mechanism and the load mechanism, it becomes a state in which a load in a direction of canceling the weight of the travel handle 20 is generated and only the weight of the travel handle 20 is applied. While, at the time of moving the travel handle 20 upward, it becomes a state in which only the weight of the travel handle 20 acts, therefore in cases where the travel handle 20 has a predetermined weight, it becomes possible to move the travel handle 20 upward and downward by an appropriate force.

Figure 6:
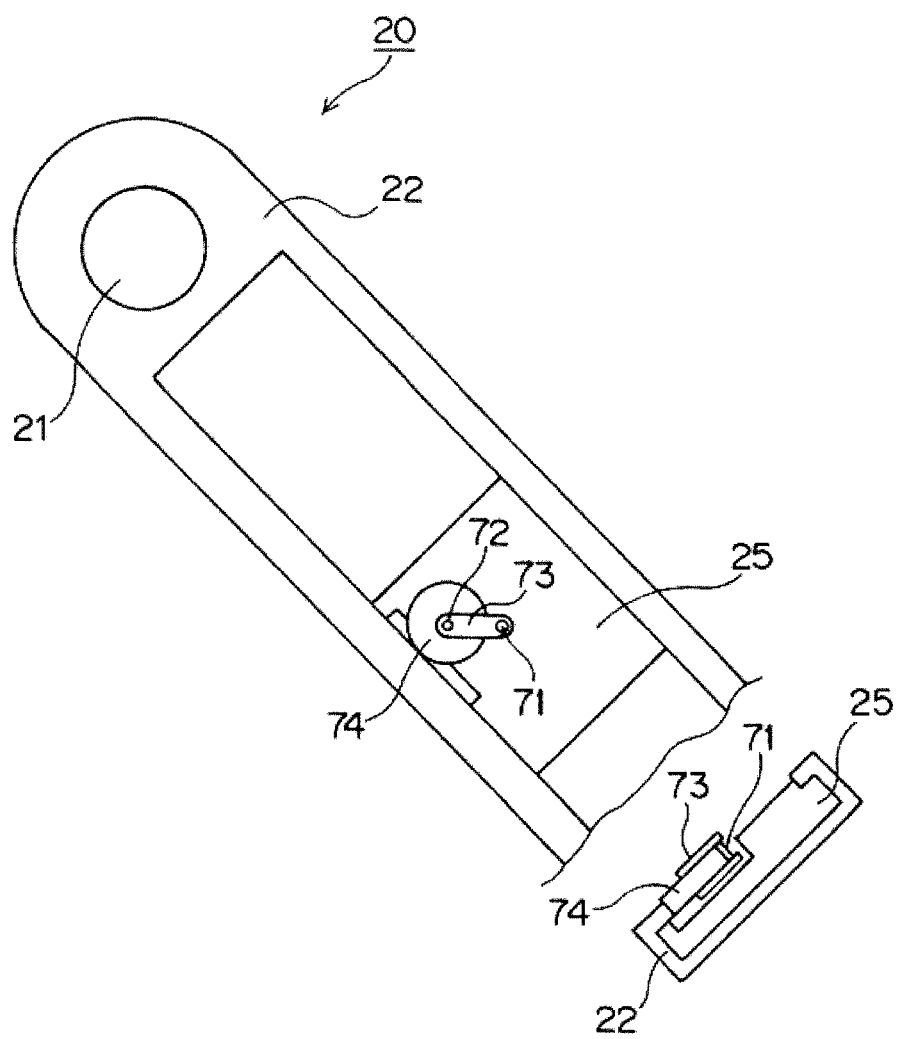
FIG. 6 is a schematic view showing a main portion of a travel handle 20 according to a second embodiment of the present invention.

Next, another embodiment of the present invention will be described. FIG. 6 is a schematic view showing the main part of the travel handle 20 according to a second embodiment of the present invention. Note that in FIG. 6, the front surface and the cross-section of the support plate 22 of the travel handle 20 are shown.

The travel handle 20 according to a second embodiment is provided with a braking roller 74 supported rotatably about a shaft 72 at a tip end of a swing arm 73 swingable about a shaft 71 provided to the slider 25 in an upright state. This braking roller 74 is composed of a metallic inner peripheral region 52 and an outer peripheral region 53 made of an elastic material such as rubber, similar to the braking roller 54 according to the above-described embodiment. Further, the braking roller 74 is provided with a load mechanism which is similar to the load mechanism according to the above-described embodiment, and is configured to apply a load against rotation.

Also in the travel handle 20 according to this second embodiment, when moving the travel handle 20 downward, an operator M tries to push the gripping bar 21 of the travel handle 20 obliquely downward. With this, by the frictional force between the outer peripheral region 53 of the elastic member of the braking roller 74 and the groove portion side surface of the support plate 22 of the travel handle 20, the swing arm 73 swings in a direction to press the braking roller 74 against the groove portion side surface of the support plate 22 of the travel handle 20. As a result, the braking roller 74 in which the outer peripheral region 53 is formed of an elastic member is deformed, so that the frictional force of the support plate 22 against the groove portion side surface of the travel handle 20 is increased, so that the weight of the travel handle 20 is holed. Then, when an operator M pushes the gripping bar 21 of the travel handle 20 obliquely downward, so that the braking roller 74 rotates in a state in which the braking roller 74 is in contact with the groove portion side surface of the support plate 22 of the travel handle 20. At this time, the braking roller 74 rotates against the braking force acted by the load mechanism similar to that of the first embodiment, the travel handle 20 is moved obliquely downward.

On the other hand, when moving the travel handle 20 upward, an operator M moves the gripping bar 21 of the travel handle 20 obliquely upward. With this, the swing arm 73 swings in a direction to separate the braking roller 74 from the groove portion side surface of the support plate 22 of the travel handle 20. With this, it becomes a state in which the braking roller 74 and the groove portion side surface of the support plate 22 of the travel handle 20 are only in contact with each other and almost no frictional force acts therebetween. When an operator M pulls the travel handle 20 obliquely upward, the travel handle 20 is moved obliquely upward against its own weight.

Figure 7:
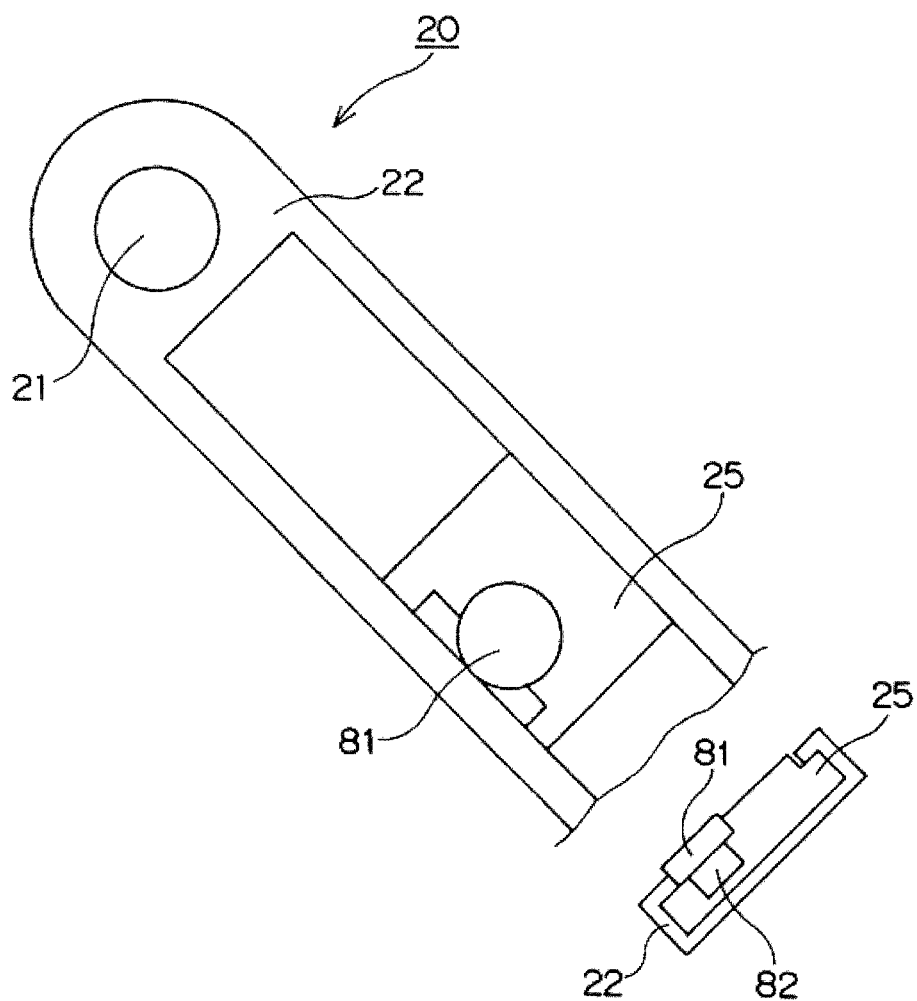
FIG. 7 is a schematic view showing a main portion of a travel handle 20 according to a third embodiment of the present invention.

Still another embodiment of the present invention will now be described. FIG. 7 is a schematic view showing a main part of a travel handle 20 according to a third embodiment of the present invention. In FIG. 7, the front surface and the cross-section of the support plate 22 of the travel handle 20 are shown.

The travel handle 20 according to this third embodiment is provided with a braking roller 81 composed of a metallic inner peripheral region 52 and an outer peripheral region 53 formed of an elastic member such as rubber in the same manner as in the braking roller 74 according to the above-described embodiment. This braking roller 81 is connected to a slider 25 via a rotary damper 82 that resists rotation in one direction of rotation and freely rotates in the other direction of rotation.

In the travel handle 20 according to this third embodiment, when moving the travel handle 20 downward, an operator M attempts to push the gripping bar 21 of the travel handle 20 obliquely downward. At this time, by the function of the rotary damper 82, a resistor is generated in the rotation of the braking roller 81 in contact with the groove portion side surface of the support plate 22 of the travel handle 20, the travel handle 20 is moved obliquely downward while receiving a predetermined resistance.

On the other hand, when moving the travel handle 20 upward, an operator M pulls the gripping bar 21 of the travel handle 20 obliquely upward. At this time, the braking roller 81 rotates without being resisted. Therefore, when an operator M move the travel handle 20 obliquely upward, the travel handle 20 is moved obliquely upward against its own weight.

It should be noted that in the above-described embodiments, although the case of moving the travel handle 20 upward and downward in the inclined direction of the travel handle 20 has been described, a structure may be configured such that the travel handle 20 is moved upward and downward in the vertical direction.

DESCRIPTION OF SYMBOLS

11: Front wheel
12: Rear wheel
20: Travel handle
21: Gripping bar
22: Support plate
24: X-ray detector
25: Slider
40: Main body
41: Support
44: X-ray tube
45: Collimator
52: Inner peripheral region
53: Outer peripheral region
54: Braking roller
55: Washer
56: Disc spring
57: Screw
60: Eccentric member
61: Rotation shaft portion
62: Flange portion
63: Shaft
64: Threaded portion
73: Swing arm
74: Braking roller
81: Braking roller
82: Rotary damper
M: Operator

The invention claimed is:

1. A mobile radiation imaging apparatus provided with a main body having wheels, a support provided to the main body in an upright posture, a radiation irradiation unit supported by the support, and a travel handle used when the main body is traveled, the mobile radiation imaging apparatus comprising:
a guide member provided to the main body to support the travel handle in an ascendable and descendable manner;
a braking roller provided to the main body in such a manner as to be in contact with the travel handle; and
a braking control mechanism configured to perform control such that braking force by the braking roller against an upward/downward movement of the travel handle is increased when the travel handle is moved downward and decreased when the travel handle is moved upward.

2. The mobile radiation imaging apparatus as recited in claim 1,
wherein the braking roller has an outer peripheral region formed of an elastic member in contact with the travel handle, and
wherein the braking control mechanism includes:
a load mechanism configured to apply a load to rotation of the braking roller; and
a swing support mechanism configured to support the braking roller in such a manner as to be swingable about a center of swing positioned lower than a contact region between the braking roller and the travel handle.

3. The mobile radiation imaging apparatus as recited in claim 2,
wherein the swing support mechanism is provided to the main body in such a manner as to be rotatable about a center of rotation positioned lower than the contact region between the braking roller and the travel handle and is composed of an eccentric member having a shaft rotatably supporting the braking roller at a position eccentric from the center of rotation, and
wherein the load mechanism is composed of a clamping member configured to clamp the braking roller between the clamping and the eccentric member with a braking force.

* * * * *